United States Patent [19]
Roy et al.

[11] Patent Number: 5,956,134
[45] Date of Patent: Sep. 21, 1999

[54] INSPECTION SYSTEM AND METHOD FOR LEADS OF SEMICONDUCTOR DEVICES

[75] Inventors: Rajiv Roy; Michael D. Glucksman, both of Plano; Weerakiat Wahawisan, Carrollton; Paul Harris Hasten, Garland; Charles Kenneth Harris, Dallas; George Charles Epp, Van Alstyne, all of Tex.

[73] Assignee: Semiconductor Technologies & Instruments, Inc., Dallas TX

[21] Appl. No.: 09/069,056

[22] Filed: Apr. 28, 1998

Related U.S. Application Data

[63] Continuation-in-part of application No. 08/890,814, Jul. 11, 1997.

[51] Int. Cl.⁶ .................................................. G01B 11/24
[52] U.S. Cl. ................... 356/237.5; 356/394; 348/126; 382/147
[58] Field of Search .................... 356/237, 394, 356/398, 375, 376; 250/548, 560, 561; 348/87, 94, 125, 126; 382/154; 29/720, 740, 833, 846

[56] References Cited

U.S. PATENT DOCUMENTS

| | | | |
|---|---|---|---|
| 3,671,726 | 6/1972 | Kerr | 235/151.3 |
| 4,199,253 | 4/1980 | Ross | 356/5 |
| 4,259,589 | 3/1981 | DiMatteo et al. | 250/556 |
| 4,686,565 | 8/1987 | Ando | 358/101 |
| 4,696,047 | 9/1987 | Christian et al. | 382/8 |
| 4,733,969 | 3/1988 | Case et al. | 356/375 |
| 4,739,175 | 4/1988 | Tamura | 250/561 |
| 4,772,125 | 9/1988 | Yoshimura et al. | 356/237 |
| 4,774,403 | 9/1988 | Arts | 250/205 |
| 4,793,707 | 12/1988 | Hata et al. | 356/375 |
| 4,872,052 | 10/1989 | Liudzius et al. | 356/237 |
| 4,891,772 | 1/1990 | Case et al. | 364/562 |
| 4,900,146 | 2/1990 | Penney et al. | 356/1 |
| 4,978,220 | 12/1990 | Abramovich et al. | 356/394 |
| 4,980,971 | 1/1991 | Bartschat et al. | 29/833 |

(List continued on next page.)

*Primary Examiner*—Hoa Q. Pham
*Attorney, Agent, or Firm*—Akin, Gump, Strauss, Hauer & Feld, L.L.P.

[57] ABSTRACT

A system for transporting and inspecting, seriatim, semiconductor devices with plural prong type or solder ball type leads includes a head for transporting the semiconductor devices from one support structure, such as a tray or tube, to a second support structure, such as a tray or tape, and wherein two dimensional and three dimensional measurements of the positional accuracy of the leads is carried out during the transport process. The inspection apparatus is interposed in the transport path and includes a first optical sensor such as a CCD camera oriented to capture a two dimensional image of the semiconductor device package and compare the image with a predetermined two dimensional image store in a central processing unit (CPU). A high intensity light source, such as a laser, generates a plane of light which is reflected off of the semiconductor device leads to a second optical sensor, also comprising a CCD camera, wherein a so-called three dimensional image is generated to be compared by the CPU with predetermined or calculated positional relationships of the leads to establish coplanarity of the lead tips, or lack thereof. The system includes a sensor located such that the semiconductor device is centered in a field of view of the cameras to capture the respective images. The transport head may be rotated to correct for improper positioning of the device prior to generation of the three dimensional image. The system may interchangeably inspect semiconductor device packages with prong leads extending from one or all sides of a rectangular substrate as well an array of solder ball leads supported on a substrate. A modified arrangement of the inspection system is adapted for inspecting multiple semiconductor devices with solder ball leads and supported on wafer type substrates.

30 Claims, 4 Drawing Sheets

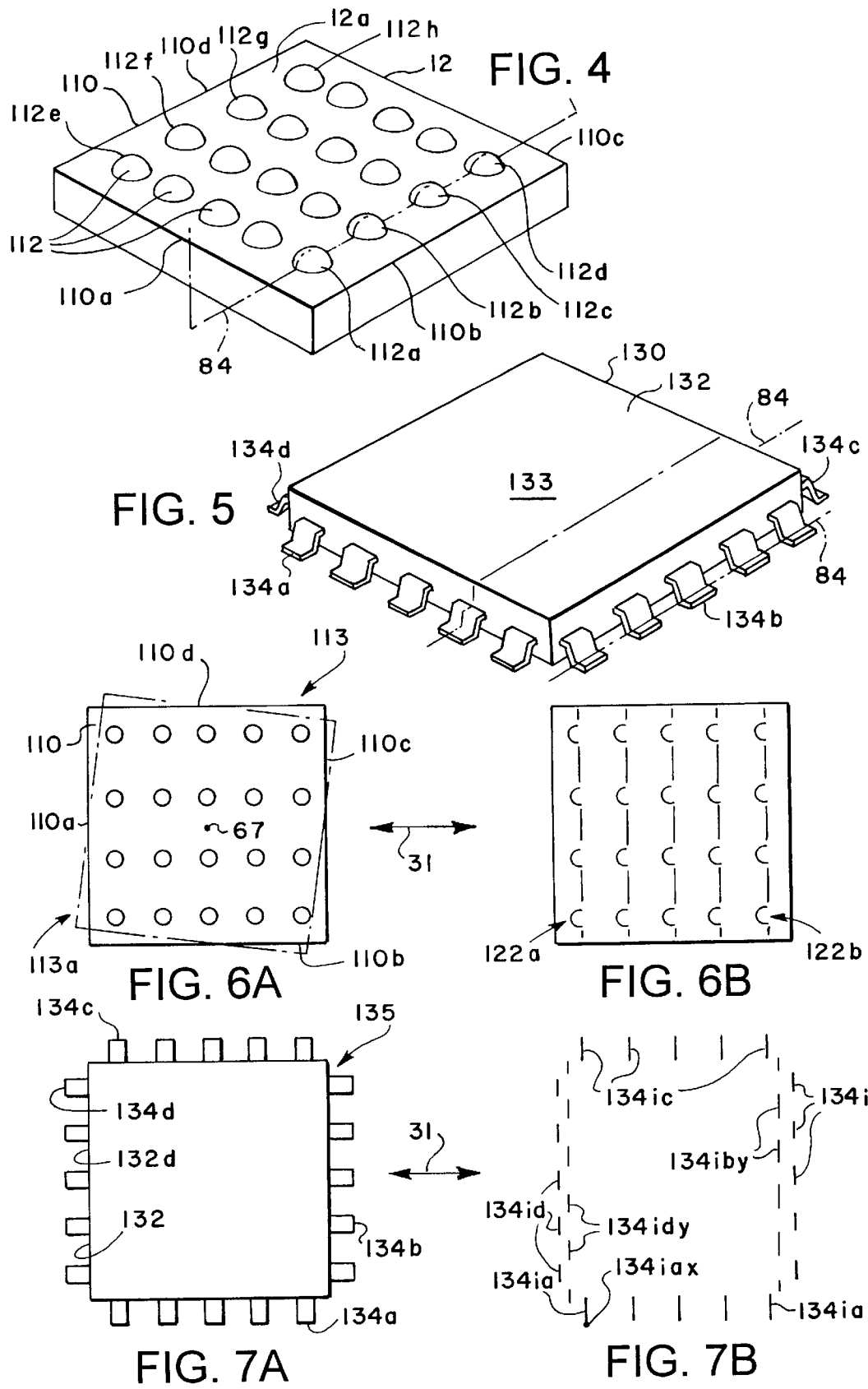

INSPECTION SYSTEM AND METHOD FOR LEADS OF SEMICONDUCTOR DEVICES

CROSS REFERENCE TO RELATED APPLICATION

This application is a continuation-in-part of copending U.S. patent application Ser. No. 08/890,814 filed: Jul. 11, 1997.

FIELD OF THE INVENTION

The present invention pertains to an inspection system and method for determining the existence and positional integrity of prong or blade type leads and solder ball type leads for semiconductor devices.

BACKGROUND

Several systems have been developed for inspecting the electrical leads of various semiconductor devices or so called "packages". Systems have been developed which measure the positional integrity of semiconductor devices which have straight or bent prong type leads extending from one or more sides of a rectangular device package and systems and methods have been developed for determining the positional integrity and coplanarity of semiconductor devices which include plural, so-called solder ball type leads arranged in an array on a surface of the device. The measurement of the coplanarity of the lead ends of prong type leads and, particularly, the coplanarity of solder ball or ball grid array devices is important in order to assure the integrity of an electrical circuit using these devices upon assembly of the devices to the circuit.

For example, systems have been developed which use back lighting of the semiconductor package and view the package with a charge coupled device or so-called CCD camera to capture an image of the leads. If leads extend from more than one side of the package or device, the device is rotated two or more times to capture an image of the other sets of leads and these images are compared to a template to determine if the leads are in a correct position. The imaging and comparison process may be carried out on a digital microprocessor or so-called central processing unit (CPU) to increase the speed and efficiency of the inspection process. This type of system can be used to take the three dimensional height measurement of semiconductor devices with so-called "gull wing" shaped prong type leads but is not suitable for measuring or inspecting devices with so called solder ball or similar type leads.

Systems have also been developed which use a combination of lasers, triangulation and a CCD camera to obtain two dimensional and three dimensional measurements of prong type leads or solder ball type leads. Typically, the semiconductor devices being measured reside in a tray or other holding structure while a laser head scans one or more leads at the same time. U.S. Provisional patent application 60/051,239 filed Jun. 30, 1997 and U.S. patent application Ser. No. 08/890,814 filed Jul. 11, 1997, both assigned to the assignee of the present invention, describe apparatus for two dimensional and three dimensional inspection of semiconductor device leads.

Still further, systems have been developed which project light from multiple sources to form shadows of the semiconductor device leads and, by measuring the length of the shadows, the three dimensional "height" information of the leads can be obtained.

Known methods and apparatus for making semiconductor device lead measurements or inspections have not been adapted for performing the inspection measurements for both two dimensional (2D) and three dimensional (3D) measurements combined, or while the device is moving from one position to another. Known apparatus also require complicated mechanisms to manipulate the devices during the inspection process and require that the device be held stationary while the inspection process is performed. Moreover, known lead inspection systems and methods have not been readily adaptable to measuring semiconductor devices or packages with both the gull wing or similarly configured prong type leads and solder ball type leads in an arrangement which requires little or no modification of the system or method during the lead inspection process.

In particular, it has been noted that known systems which rely on a combination of lasers and triangulation to obtain the three dimensional height or coplanarity measurement of a lead array can be particularly sensitive to the reflectivity of the lead material, which may vary considerably depending on the material used for the leads, the degree of oxidation of the lead material or other conditions which might affect the reflectivity of the lead surface.

Accordingly, there has been a continuing need to develop an inspection system and method for inspecting the electrical leads of semiconductor packages of both the prong type as well as the solder ball type without requiring substantial modification to the system when measuring one type versus the other while making measurements with accuracy, regardless of the reflectivity characteristics of the lead material. Moreover, there has also been a need to develop a system and method which is capable of measuring the leads of semiconductor devices more efficiently and expeditiously, particularly considering the massive quantities of such devices that are manufactured at substantial production rates. In this latter regard there has been a need to develop an inspection system and method which may be interposed in a production process at some stage between the finished fabrication of the semiconductor device and its application to an electrical circuit. It is to these ends that the present invention has been developed.

SUMMARY OF THE INVENTION

The present invention provides an improved system and method for measuring the existence and positional integrity of electrical leads of semiconductor devices and the like.

In accordance with one aspect of the present invention, a semiconductor device lead inspection system is provided which is interposed in a production process for transferring multiple semiconductor devices from one transport or handling structure to another without interrupting or slowing the production or transfer process. In particular, the invention contemplates the arrangement of a lead inspection system and method wherein the system is disposed on an apparatus which is operable to transfer semiconductor devices from one handling or holding structure, such as a tray, to another handling or holding structure, such as an elongated tape. The inspection process is carried out without delay during the transfer process.

In accordance with another aspect of the present invention, a lead inspection system is provided which is operable to make both two dimensional (2D) and three dimensional (3D) measurements of semiconductor packages while there is relative movement between the lead inspection system and the semiconductor packages or devices. The system may be advantageously incorporated in a transfer machine which is operable to transfer semiconductor devices from handling or storage structures such as tubes or trays to other handling or storage structures, such as tapes or other tubes or trays. Since there is a need in the production process to pick a semiconductor package or device out of one of these types of handling structures and move it to a different handling structure, the arrangement of the system for performing the lead inspection while the transfer is occurring is particularly advantageous and does not require any special staging or a separate station to perform the inspection.

In accordance with another aspect of the present invention a lead inspection system for both prong type leads and solder ball leads on semiconductor packages is provided which includes a sensor located such that the semiconductor package or device will be located in a field of view for a first CCD camera and a high intensity light for making 2D inspection measurements by capturing an image of the package. This image is then transferred to a frame grabber in a central processing unit (CPU) which computes an "x" and "y" location of the leads. In addition, a rotational position or orientation is computed to account for any errors in the rotational position of the lead caused by the storage structure or handling and transfer mechanism. The mechanism handling the conductor package then adjusts the rotational position of the device to place the leads in a proper orientation with respect to a second sensor which detects the position of the device for making a so-called three dimensional (3D) or height measurement of the leads. Still further, the system monitors the position of the semiconductor device relative to a laser which is operable to expose the device to a plane of light essentially perpendicular to the plane of the semiconductor package and the laser is energized to emit a light beam which is reflected into the lens of a second CCD camera. The displacement of the laser line projected to the second camera provides information of the height of the solder ball or prong leads of the device from which calculations may be made by the CPU to determine coplanarity of the leads.

The system of the present invention also provides the flexibility of being able to inspect a semiconductor device in a variety of orientations. The inspection system may be adapted to various semiconductor device handling or transport systems, for example. Moreover, the inspection system is easily adapted to inspect leads of various sizes of semiconductor devices including very small semiconductor devices fabricated individually or fabricated on large substrates and wherein measurement of the leads, such as solder ball type leads, is carried out before the devices are separated from each other, if such is to be done.

Those skilled in the art will further appreciate the above-mentioned advantages of the invention together with other important aspects thereof upon reading the detailed description which follows in conjunction with the drawing.

BRIEF DESCRIPTION OF THE DRAWING

FIG. 4 is a perspective view of a semiconductor device comprising a ball grid array (BGA) showing the array of solder ball leads thereon;

FIG. 5 is perspective view of a semiconductor device having gull wing prong type leads extending from all four sides of a rectangular substrate or package portion of the device;

FIG. 6A is a representation of the two dimensional (2D) image of the device of FIG. 4;

FIG. 6B is a representation of the three dimensional (3D) image of the device of FIG. 4;

FIG. 7A is a representation of the 2D image of the device of FIG. 5;

FIG. 7B is representation of the 3D image of the device of FIG. 5;

DETAILED DESCRIPTION OF PREFERRED EMBODIMENTS

Figure 1:
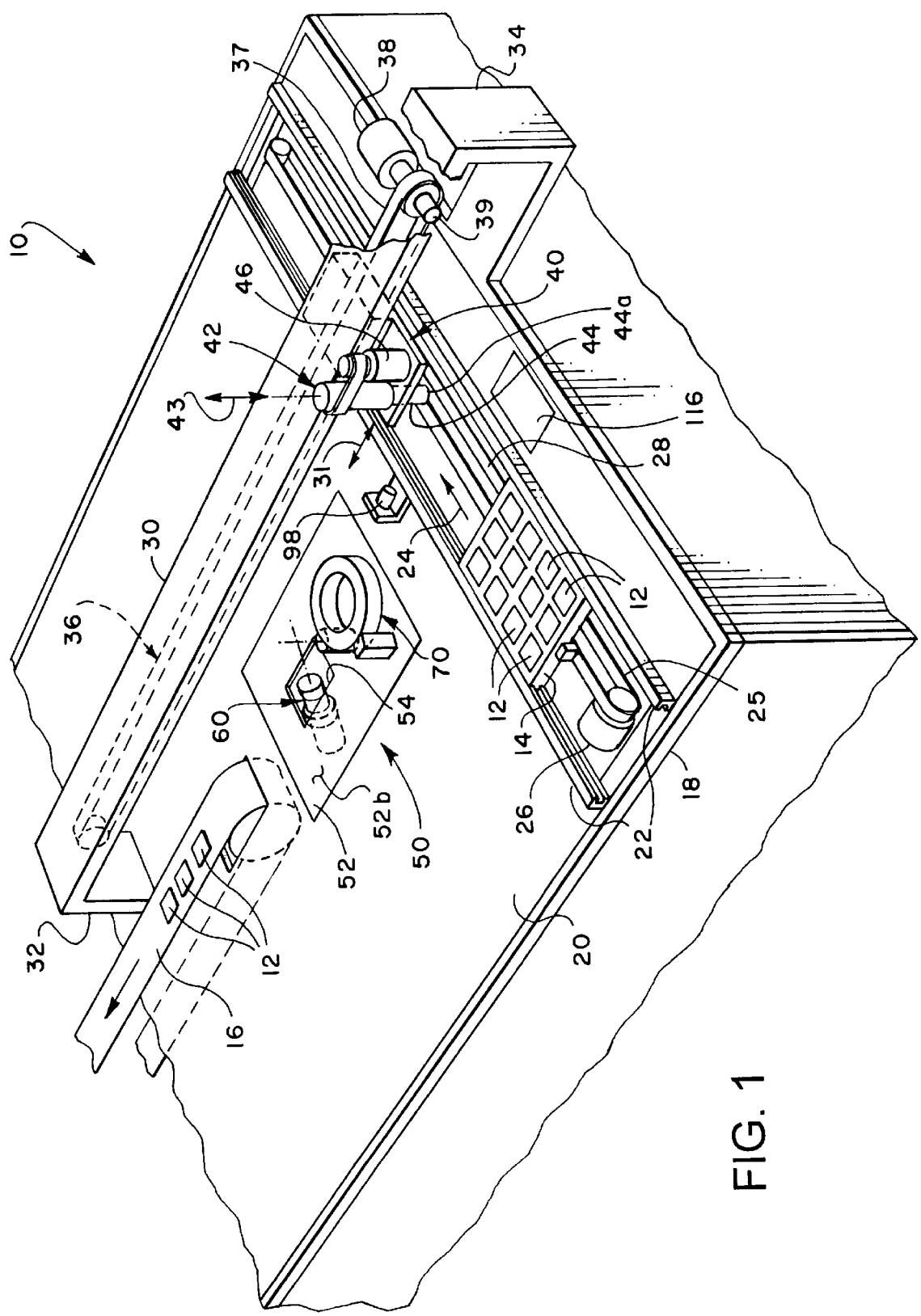
FIG. 1 is a perspective view, in somewhat simplified or schematic form, of a semiconductor device handling or transfer apparatus including the lead inspection system of the present invention.

In the description which follows like parts are marked throughout the specification and drawing with the same reference numerals, respectively. The drawing figures are not necessarily to scale and certain elements may be shown exaggerated in scale or in somewhat schematic form in the interest of clarity and conciseness.

Referring to FIG. 1, there is illustrated a system in accordance with the invention, including a portion of an apparatus 10 for transferring semiconductor devices or so called packages from one handling structure or media to another. In particular, the embodiment of the apparatus 10 illustrated somewhat schematically in FIG. 1 is operable to transfer a plurality of semiconductor devices or packages 12 from an elongated, generally rectangular support or handling media comprising a tray 14 to another support structure or handling media comprising an elongated flexible tape 16, both structures being well known in the art of semiconductor devices, whereby the devices are prepared for handling in the fabrication of certain circuit components utilizing the devices. By way of example, the semiconductor devices 12 are provided with solder ball type leads and will be described further herein. The semiconductor devices 12 may also be of a type which comprise a plurality of prong type leads projecting from one or more sides of a rectangular base or substrate and may be configured to have a so-called gull wing shape when viewed in cross section. Typically the tips of the leads must meet a strict requirement of true position and coplanarity, as understood by those skilled in the art. Semiconductor devices transferable by the apparatus 10 may comprise other configurations of so-called ball grid arrays (BGA) wherein plural somewhat hemispherical solder ball leads are supported in a predetermined array on a planar portion of the device package or substrate. Examples of semiconductor devices generally of the types described above will be described in further detail hereinafter.

By way of example, the apparatus 10 includes a frame 18 having a generally horizontally oriented rectangular planar top surface 20. Suitable support structure 22 comprising opposed elongated rails or the like is provided for supporting the tray 14 for linear traversal in the direction of arrow 24 from a point wherein the tray is loaded into the support structure. A storage magazine, not shown, for multiple trays 14 may be provided together with suitable mechanism for moving the trays 14 onto the support structure 22. The support structure 22 also includes a suitable traversing mechanism 25 for moving the trays 14 in the direction of the arrow 24 linearly, such traversing mechanism including a precision controlled motor 26, for example. The motor 26 may be suitably connected to an endless belt or chain drive mechanism 28 engageable with a tray 14 or a suitable support member therefor, not shown, for moving the tray along the support structure 22 into a position under an overhead frame member 30 extending between two spaced apart column portions 32 and 34. The overhead frame member 30, is spaced a suitable distance above surface 20 and supports suitable linear traversing mechanism 36 which may comprise an endless belt or chain drive 37, by way of example, drivenly connected to a precision controlled motor 38. The traversing mechanism 36 is operably connected to a support member 40, suitably mounted on the frame member 30 for linear traversal therealong in opposite directions, as indicated by the path arrow 31, and normal to the path of movement of tray 14.

The support member 40 is suitably mounted on the frame 30 for the aforementioned movement and is also adapted to support a pickup and holding device 42 for removing a semiconductor device 12 from a selected recess in tray 14 and transporting the semiconductor device to the transport and support tape 16 for placement thereon, as indicated by the positions of some of the semiconductor devices 12 already placed on the support structure or tape 16. The pickup and transport device 42 includes a telescoping head portion 44 which is operable to move in opposite directions along an axis depicted by the arrow 43 in FIG. 1 for extending toward tray 14 to engage a semiconductor device 12, remove the device from the tray 14 and hold the device in a desired position until it is moved and deposited on the handling media or tape 16. A suitable precision controlled motor 46 is disposed on the support member 40 and is suitably connected to the pickup device 42 for rotating the pickup head 44 about central axis 43 in opposite directions to properly orient a device 12 in a desired rotative position. Those skilled in the art will appreciate that the motors 38 and 46 may be suitably controlled in conjunction with operation of the motor 26 to successively place semiconductor devices 12 supported on tray 14 in a position to be picked up and held by the pickup head 44, rotated to a desired position about the central axis 43 of the pickup head and then transported to a position to deposit a device 12 on the support structure or tape 16. The pickup head 44 may, for example include a suitable orifice at its distal end 44a connected to a source of vacuum, not shown, for providing a pickup and holding force on a semiconductor device 12. Once a semiconductor device or package 12 has been removed from tray 14 and placed on the tape 16, the support member 40 is returned to a starting position to pick up another semiconductor device from the tray 14. An encoder 39 is operably connected to mechanism 36 for providing signals to indicate precisely the position of head 44 along the path indicated by arrow 31. This process is repeated until the tray 14 is empty whereupon the tray is then moved to a parked position or removed from the apparatus 10 and another tray of semiconductor devices is placed in a working position on the support structure 22 and operably controlled by the motor 26 to be positioned under the support member 40 for sequential removal of semiconductor devices therefrom. Although the tray 14 may be moved by mechanism 25 under head 44 for pickup of devices 12 seriatim by movement of support member 40 only along path 31, the support member 40 may also be suitably mounted on member 30 for controlled movement in opposite directions normal to path 31 for removing devices 12 from tray 14.

Figure 2:
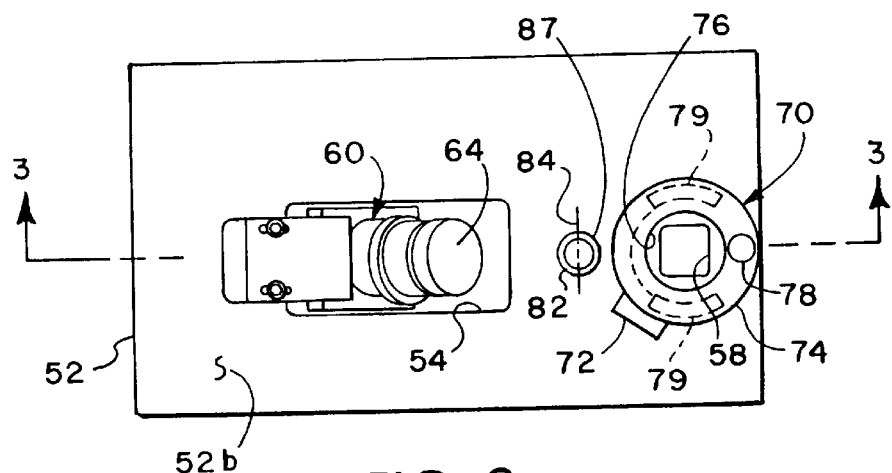
FIG. 2 is a plan view of the lead inspection system portion of the apparatus shown in FIG. 1.
Figure 3:
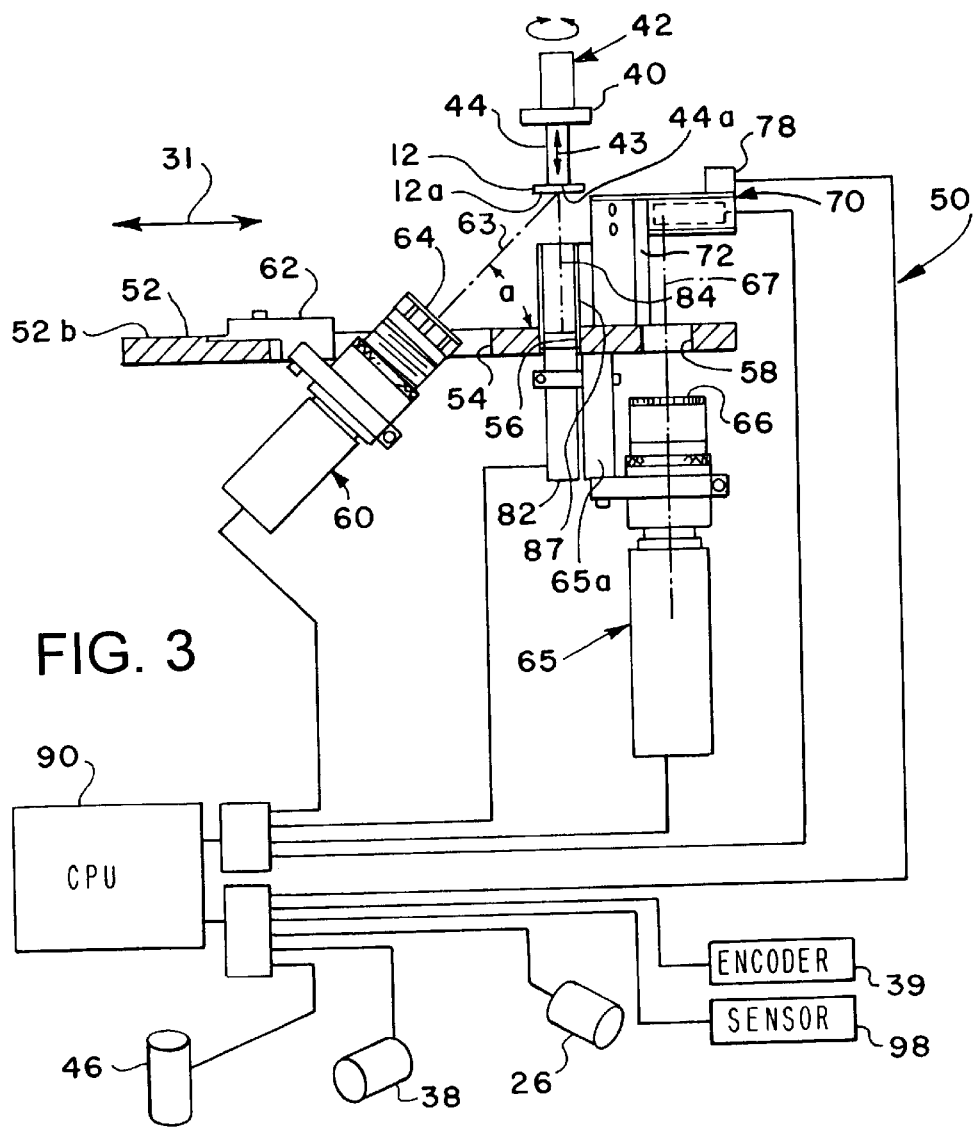
FIG. 3 is a section view taken generally from the line 3—3 of FIG. 2 and showing further components in somewhat schematic form.

While a semiconductor device 12 is being moved by the apparatus 10 between the tray 14 and the tape 16, inspection of the conductor leads of the device is carried out in combination with the transport and handling process in an efficient and rapid manner. In this regard, an inspection system including an apparatus 50, see FIGS. 1 through 3, is disposed in a position on the apparatus 10 to make a 2D and 3D inspection of a semiconductor device 12 to determine if its conductor leads are in a proper position with respect to each other and the lead support structure and to determine if the ends of the leads or surfaces of the leads which are going to be placed in contact with certain circuit elements are substantially coplanar, for example. The apparatus 50 is disposed on the apparatus 10 in a position such that the support member 40 and the pickup and transport head 44 are disposed for movement directly over the apparatus 50 so that the aforementioned inspections can be carried out. As shown in FIGS. 2 and 3, the apparatus 50 includes a generally rectangular planar, plate-like frame member 52 disposed parallel to path 31 and having plural spaced apart openings 54, 56 and 58 formed therein. A suitable optical sensor such as a CCD camera 60 is mounted at an acute angle "a" of approximately 45°, FIG. 3, with respect to the plane of the support plate 52 and is suitably supported thereon by a bracket 62 for projection through the opening 54. The camera 60 has a suitable light receiving lens 64 supported thereon and positioned with respect to the linear travel path 31 of pickup head 44, FIG. 3, such that a semiconductor device 12 supported by the pickup head 44 may be visually inspected by the camera 60.

The apparatus 50 includes a second optical sensor comprising a CCD camera 65 mounted on and beneath the support plate 52 and aligned with the opening 58 for capturing an image of the surface 12a of the semiconductor device 12 as well as any portions thereof facing downward, viewing FIG. 3. The camera 65 is mounted on a suitable bracket 65a connected to the support plate 52 and includes a suitable lens 66 for receiving light projected through the opening 58. The lens 66 has a central axis 67 extending substantially normal to the plane of the support plate 52 and the surface 12a and, thus, also extending at an angle of about 45° with the respect to the axis 63 of the lens 64.

Referring further to FIGS. 1 through 3, and primarily FIG. 3, a high intensity light source 70 is supported above the surface 52b, of the support plate 52 on a suitable bracket 72 and is characterized by a substantially ring shaped shield 74, FIG. 2, having a central opening 76 formed therein and aligned with the opening 58. One or more high intensity light sources 79, two shown in FIG. 2, are supported in the shield 74 and are operable to illuminate the surface 12a of the semiconductor device 12, as well as the entirety of any portion of a semiconductor device facing the lens 66, when such device passes over the opening 58 and 76 and is substantially centered with respect to the axis 67 so that the camera 65 may capture an image of the device.

Accordingly, the support member 40, FIG. 1, for the pickup head 44 may be traversed over the opening 58, aligned substantially with the axis 67 whereupon a suitable sensor 78, FIGS. 2 and 3, will detect the presence of the semiconductor device substantially centered in the opening 58 and the opening 72 whereupon the light source 70 will be briefly energized to completely illuminate the surface 12a of the device 12 while allowing the camera 65 to capture an image thereof The image captured by camera 65 is transmitted to a central processing unit (CPU) 90, FIG. 3, and compared to a prescribed image of the device 12 stored in a suitable memory circuit therein. After the camera 65 captures an image of the device 12, the rotative position of the device with respect to the axis 43 of the pickup head 44 will be compared to a preferred orientation of the device with respect to such axis and the CPU 90 may issue a command signal whereby the pickup head 44 will be suitably rotated by the motor 46 to properly orient the device 12 in a desired position. Once this task has been completed the semiconductor device 12 is then moved to a series of positions along path 31, one shown in FIG. 3, wherein a high intensity light source, such as a laser 82, is operable to project a planar beam 84 on and normal to the plane of the surface 12a of the device 12 to allow the camera 60 to receive a suitable well-defined reflection from conductor leads on the device to make further measurements of the actual positions of such leads. As the semiconductor device 12 is passed over the laser beam 84 images of the conductor leads on the semiconductor device are captured by the camera 60 and such images are communicated to the central processing unit (CPU) 90, see FIG. 3, for processing thereby. The high intensity light source or laser 82 comprises a tubular shield 87, FIG. 3, together with a source of a generally planar sheet-like beam 84 of radiated energy which extends parallel to the axis 67 and also intersects the axis 63 at an angle of about 45°. The arrangement of laser light source 82 normal to the surface 12a of the semiconductor device 12 and the camera axis 63 at an acute angle with respect to such surface provides a more accurate image of the device and its associated leads.

As shown in FIG. 3, the CPU 90 is suitably operably connected to the camera 60, the camera 65, the light source 70 and the light source or laser 82 for controlling the operation of these elements. Images transmitted from the cameras 60 and 65 are compared to preprogrammed images in a suitable program stored in the CPU 90 whereby the images viewed by the cameras 60 and 65 are compared to these prestored images and the semiconductor device 12 is either passed as having a suitable configuration of its leads or rejected by the inspection apparatus 50. The CPU 90 or a suitably linked CPU, not shown, may be used to control the motors 26, 38 and 46 and also control the pickup and holding action of the pickup head 44. Suitable sensors, including the sensor 78, the encoder 39 and a sensor 98, FIG. 1, may be appropriately located on the apparatus in positions as indicated for sensor 98 and encoder 39. Sensor 98 is operable to determine the position of tray 14 so that the motor 26 may be controlled to properly position a semiconductor device 12 under the pickup head 44. The encoder 39 is operable to determine the position of the support member 40 for positioning the pickup head 44 to engage a semiconductor device 12 and remove it from the tray 14 and sensor 78 is operable to determine when a semiconductor device 12 supported by the pickup head 44 is at a predetermined position with respect to the light source 70. Sensor 78, operating in conjunction with CPU 90 and encoder 39, also provides for positioning a semiconductor device 12 to be illuminated by laser source 82 at desired intervals. For a given type and size of semiconductor device 12, the encoder 39 is operable, in conjunction with CPU 90, to determine successive positions of the device along path 31 and control energization of laser 82 when leads to be inspected can be intersected by beam 84. The sensors 39, 78 and 98 may be operated in conjunction with a program stored in the CPU 90 or a suitably linked CPU, not shown, for a particular type of semiconductor device so that the device can be properly oriented and the light sources 70 and 82 suitably energized to inspect the leads of the semiconductor device.

Referring now to FIG. 4, there is illustrated a semiconductor device 12 inverted with respect to the position the device would assume in FIGS. 1 through 3. The semiconductor device 12 is shown in an inverted position with respect to that shown in FIG. 3 for clarity and comprises a so-called ball grid array (BGA) type device comprising a generally rectangular planar substrate 110 on which are supported solder ball leads 112 positioned in a predetermined array of columns and rows, for example, and projecting from surface 12a of the substrate. The solder balls 112 are adhered to pads, not shown, which are suitably connected to conductors of an integrated circuit disposed within the substrate 110 in a known manner. The device 12 is adapted to be secured to a suitable circuit board or element, not shown wherein the distal surfaces of the solder ball leads 112 contact coplanar conductor pads on such circuit board, for example. Accordingly, it is important when inspecting the leads 112 that their proper position with respect to each other and the substrate 110 be verified, that the presence of all leads be verified and that the coplanarity of the leads be verified so that, when the device 12 is assembled to a circuit, all leads make contact with their corresponding conductors. FIG. 6A, for example, illustrates an image 113 received by the camera 65 when the device 12 is positioned over the light source 70 and generally centered with respect to the axis 67. When an image is captured by the camera 65 it is compared to a "template" forming part of a program stored within the CPU 90 and, if the position of a lead 112 with respect to another lead or one or more of the side edges 110a, 110b, 110c, 110d of the substrate 110 is not verified the device 12 may be rejected. Upon rejection, if such occurs, the support member 40 may be traversed to a suitable position to release the semiconductor device 12 for recycling or scrapping, as the case may be. For example, the support member 40 may be traversed by mechanism 36 to a position where the pickup head 44 may deposit a rejected semiconductor device into a tray or receptacle 116, FIG. 1. Other treatments of a semiconductor device inspected by the apparatus 50 may, of course, be carried out, if desired.

If a device 12 whose image, as shown in FIG. 6A, is not properly oriented about the axis 67 to be aligned with, for example, the path of traversal indicated by the arrow 31, the CPU 90 measures the angular error by comparing the image 113 of FIG. 6A, with the aforementioned template stored within the CPU 90 and issues a command to the motor 46 to rotate the pickup head 44 to orient the device 12 in a prescribed position. The image could be skewed, for example, as indicated at 113a, FIG. 6A indicating the device 12 requires to be rotated back to the position indicated by image 113. This step is carried out before the pickup head 44 moves to the position shown in FIG. 3, at which position the planar, sheet-like laser beam 84, see FIG. 4, also, is projected on a set of solder ball leads 112a through 112d, for example, and a reflection of the projected light beam is captured by the camera 60 as an image.

The images of a row of solder ball leads 112, as viewed by the camera 60, is indicated at 122a in FIG. 6B. As the pickup head 44 moves further to the left, viewing FIG. 3, successive rows of solder ball leads 112 are imaged by the camera 60 and a composite image, as shown in FIG. 6B, is provided. The first and last images of solder ball leads 112 are referenced in FIG. 6B wherein a row of solder ball leads 112a to 112d is indicated by the image 122a and a row of leads 112e through 112h is indicated as an image 122b. The actual number of leads may be substantially greater or less and arranged in a variety of patterns other than shown in the exemplary views of FIGS. 4, 6A and 6B, and only a representative number of leads are indicated for the sake of clarity and conciseness. The so-called height of the solder ball leads, as indicated by the images in FIGS. 6B, may be compared to a template stored in a suitable memory portion of the CPU 90, or calculated using a suitable program wherein the heights of each solder ball lead may be compared, with respect to its position in the array, to determine if a plane will be established in which all solder ball leads will contact the surface of such plane. Accordingly, it is not absolutely necessary that each solder ball lead have the same height above the substrate 110 but it is important that the tips of the solder ball leads which will contact the aforementioned circuit board all lie in a particular plane, There may, of course, be suitable tolerance limits on the lack of parallelism between the substrate 110 and such a plane, if desired.

Measurement and comparison techniques similar to those described in the aforementioned patent applications may be used in determining the positional accuracy of the respective leads 112. If coplanarity of the leads 112 cannot be established then the semiconductor device 12 is rejected, preferably in the manner described above, and the next semiconductor device being processed by the apparatus 10 is subjected to the inspection process described herein.

Referring now to FIG. 5, another semiconductor device or package which may be inspected by the system of the present invention is illustrated and generally designated by the numeral 130. The device 130 is of type wherein a generally rectangular, planar box shaped substrate 132 is adapted to support opposed sets of prong type semiconductor leads, sometimes referred to as gull wing leads and indicated by the numerals 134a, 134b, 134c and 134d. The representation of the device 130 in FIGS. 5, 7A and 7B is somewhat schematic and the total number of leads projecting from each side of the substrate 132 may be substantially greater than that indicted. In FIG. 5, the device 130 is oriented in the same direction that it would be when facing the cameras 60 and 65. In other words, the pickup head 44 would engage the surface 133 of the substrate 132 whereas, as previously mentioned the pickup head 44 would engage a surface on the substrate 110 opposite but generally parallel to the surface 12a from which the solder balls 112 project.

Referring to FIG. 7A, there is illustrated an image 135 of the semiconductor device 130 as captured by the camera 65 when the device is passed over the central opening 76 in the light shield 74 and illuminated by the light source 70. This image is compared to a template, not shown, suitably stored in a program in the CPU 90. The image 135 of FIG. 7A shows the positions of the rows of leads 134a through 134d with respect to the substrate 132 and if a lead is missing or out of position in the projection of the 2D image shown the device 130 may be rejected by the apparatus 10.

However, in order to determine the coplanarity of the tips of the leads 134a through 134d, the device 130 is also moved past the light source or laser 82 and reflected images of beam 84 are captured by the camera 60. FIG. 7B shows a typical array of images of the set of leads 134a, as indicated by the lines 134ia while a set of lines 134ib indicates an image from the set of leads 134b. In like manner a set of images 134ic is that produced by the set of leads 134c and the images 134id are those produced by the set of leads 134d. For example, if the images 134ib are not a predetermined distance from the image 134iby, corresponding to the edge of the substrate 132, it is known that the lead corresponding to that image may be bent out of a plane in which all lead tips should be disposed. A corresponding verification of the position of each lead image for the sets of leads 134d is carried out as the device 130 is passed over the laser source 82.

With respect to determining the positional accuracy to the leads of the sets of leads 134a and 134c, for example, the edge 132d of the substrate 132 is used as a reference. Referring to FIG. 7B, if the tip 134iax of an image 134ia, for example, when superimposed on the image of the lead 134a of FIG. 7A does not fall in the same position, then it is determined that the planarity of the lead in question of the set 134a is not proper. This comparison process is carried out for each of the leads of the sets of leads 134a and 134c by a suitable program controlled by the CPU 90. If a tip of a lead in FIG. 7B does not coincide with the position of the tip of the same lead shown in FIG. 7A, the semiconductor device is rejected.

Those skilled in the art will appreciate from the foregoing description that a system comprising the apparatus 10 and the inspection apparatus 50 is operable to more efficiently, and with greater speed, process semiconductor devices or packages of the types described herein while inspecting the packages for the accuracy of the positions of the package leads. The CPU 90 may be suitably programmed to inspect packages of the two general types described herein, interchangeably, without requiring that the packages or devices be handled in any complex manner, other than that required for transferring the devices from one support or handling media or structure to another. Moreover, the inspection apparatus 50 is not in any way obtrusive with regard to the configuration or operation of the apparatus 10.

Figure 8:
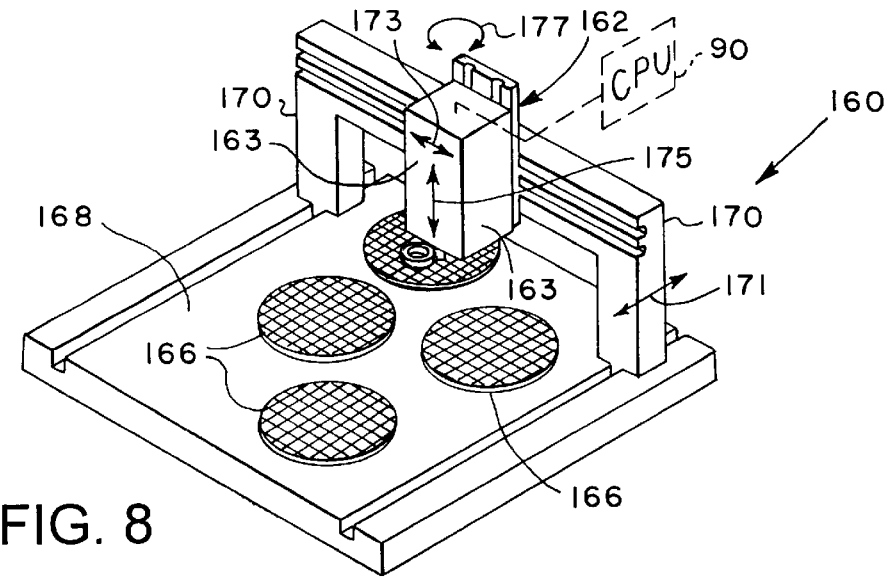
FIG. 8 is a perspective view of an alternate embodiment of a lead inspection system of the present invention for inspecting leads on so-called flip chips.
Figure 9:
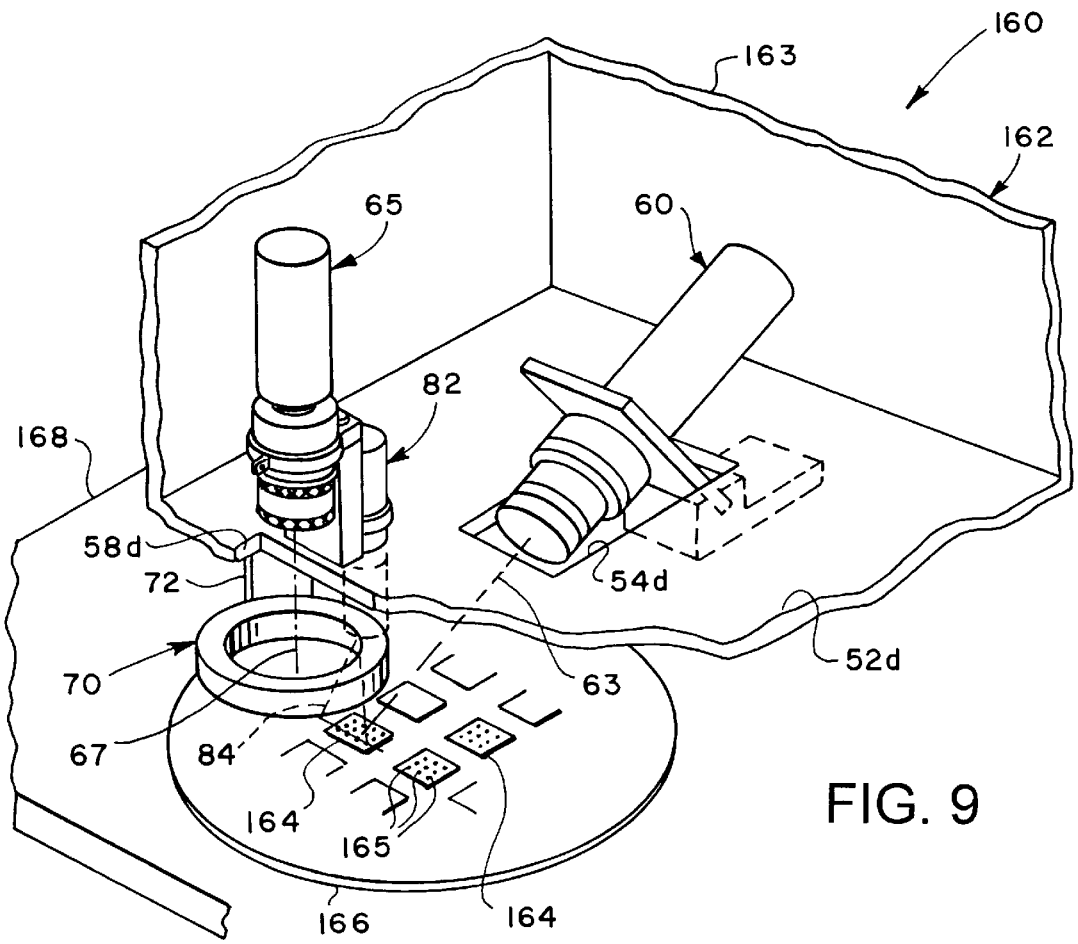
FIG. 9 is a detail perspective view, partially sectioned, on a larger scale of a portion of the system shown in FIG. 8.

Referring now to FIGS. 8 and 9, another embodiment of a system in accordance with the invention is illustrated and generally designated by the numeral 160. In the embodiment of FIGS. 8 and 9, an inspection apparatus 162 is adapted to inspect the presence of and positional accuracy of an array of solder ball leads on relatively small integrated circuit devices 164, see FIG. 9, which are disposed on a wafer type substrate 166 from which the integrated circuit devices 164 are fabricated. The circuit devices 164, sometimes known as flip chips, may be arrayed on the substrate 166 in a substantial quantity, between fifty and several hundred, for example. In the embodiment of FIGS. 8 and 9, the wafer substrates 166 may be arranged on a suitable support structure 168 which may move relative to a support frame 170 for the inspection apparatus 162. For example, the support structure 168 may be configured such that the frame 170 moves linearly relative to the wafers 166 in the direction of the double headed arrow 171 and the apparatus 162 may move on and relative to the frame 170 in the directions indicated by the arrows 173, 175 and 177. The directions of movement indicated by arrows 171, 173 and 175 are mutually perpendicular.

As shown in FIG. 9, the inspection apparatus 162 utilizes the elements of the inspection apparatus 50 comprising a support plate 52d similar to the support plate 52 but comprising part of an enclosure 163 for the apparatus 162 and inverted with respect to the arrangement of the support plate 52, so that the camera 60, the camera 65, the light source 70 and the laser or light source 82 are all in an inverted position with respect to the device to be inspected, as compared with the arrangement of the apparatus 10. However, the apparatus 162 can be suitably connected to a CPU 90 in essentially the same manner as the apparatus 50. Accordingly, the apparatus 162 can be positioned with respect to a group of devices, such as the devices 164 mounted on a wafer-like substrate 166 and operated to scan each device to determine the positional accuracy of leads 165 thereon, FIG. 9, utilizing the same methodology as the apparatus 50. Initial positioning of the apparatus 162 with respect to the support structure 168 may be dictated by positional considerations concerning the whereabouts of the substrates 166. However, the articles or substrates 166 may be placed in predetermined positions on the structure 168 or, if traversing thereon, may be placed in predetermined positions relative to the frame 170 and, with known dimensional input signals provided to the CPU 90, the apparatus 162 may be moved to a position with regard to a particular reference point on a substrate 166 prior to beginning the lead inspection process. Moreover, those skilled in the art will recognize that the apparatus 162 is operable, equally as well as the apparatus 50, when placed in an inverted position with respect to the position of the apparatus 50 and placed on structure which will enable movement of the apparatus 162 relative to the semiconductor devices 164, such that each device may be suitably inspected.

The construction and operation of the systems described hereinabove is believed to be within the purview of one skilled in the art of semiconductor device inspection systems. Conventional materials, elements and methods may be carried out in implementing the invention as regards those features and specific identifications not set forth herein. Advantages of the invention are also believed to be clearly recognizable to those skilled in the art from the foregoing description, including those which have been pointed out previously herein.

Although preferred embodiments of the invention have been described in detail, those skilled in the art will also recognize that various substitutions and modifications may be made without departing from the scope and spirit of the appended claims.

What is claimed is:

1. A system for transporting semiconductor devices from one point to another, said semiconductor devices including a plurality of leads thereon, the existence of which and the positional accuracy of which is to be determined, said system including:

a transport apparatus including a frame;

a head operable to engage and support a semiconductor device and move said semiconductor device from one position to another with respect to said frame; and a lead inspection apparatus mounted on said frame and interposed in a path of movement of said semiconductor device, relative to said lead inspection apparatus, said lead inspection apparatus being operable to inspect the existence of said leads on said semiconductor device, the positional accuracy of said leads in two dimensions with respect to a substrate of said semiconductor device and the positional accuracy of said leads with respect to a predetermined plane, while moving said semiconductor device from said one position to said another position, said inspection apparatus including:

a first optical sensor and a first light source for illuminating said semiconductor device to generate a two dimensional image by said first optical sensor;

a second light source and a second optical sensor disposed to generate a third dimensional image of said semiconductor device; and a processing unit operably connected to said first and second optical sensors for comparing images generated thereby, respectively, with information stored in said processing unit for determining the existence of leads on said semiconductor device, the positional accuracy of said leads on said semiconductor device and the coplanarity of at least portions of said leads on said semiconductor device.

2. The invention set forth in claim 1 wherein:

said inspection apparatus is positioned between a first support structure for said semiconductor device and a second support structure for said semiconductor device and said system includes support means for said head for traversing said head between said first support structure and said second support structure.

3. The invention set forth set forth in claim 2 wherein:

said system includes motor means for moving said head along a substantially linear path between said first support structure and said second support structure and motor means operably connected to said head for orienting said semiconductor device supported by said head in a predetermined position upon generating said two dimensional image.

4. The invention set forth in claim 3 wherein:

said first optical sensor is operably connected to said processing unit for comparing said two dimensional image with a predetermined image of said semiconductor device to determine the existence of and the positional accuracy of said leads on said semiconductor device in two dimensions.

5. The invention set forth in claim 4 wherein:

said processing unit is operably connected to said head for causing said head to orient said semiconductor device in said predetermined position upon making said comparison of said two dimensional image with said predetermined image.

6. The invention set forth in claim 5 wherein:

said first optical sensor comprises a CCD camera.

7. The invention set forth in claim 6 including:

a sensor for energizing said first light source when said semiconductor device is moved to a predetermined position by said head with respect to said first optical sensor.

8. The invention set forth in claim 5 wherein:

said second light source is operable to generate a generally planar beam projected onto said semiconductor device and said second optical sensor is disposed in a position to receive and transmit an image generated by said second light source as a reflection from said semiconductor device for determining the positional accuracy of plural leads on said semiconductor device with respect to each other for determination of coplanarity of said leads.

9. The invention set forth in claim 8 wherein:

said processing unit includes information stored therein which is operable to enable said processing unit to compare the positions of respective ones of said leads as determined by said image generated by said second light source and said second optical sensor to determine said coplanarity.

10. The invention set forth in claim 9 wherein:

said second light source and said second optical sensor are disposed downstream of said first light source and said first optical sensor in relation to the direction of movement of said semiconductor device connected to said head as said head is transporting said device between said support structures.

11. The invention set forth in claim 9 wherein:

said second optical sensor is a CCD camera.

12. The invention set forth in claim 1 wherein:

said first optical sensor is disposed for receiving an image projected normal to a predetermined plane of said semiconductor device.

13. The invention set forth in claim 12 wherein:

said second light source is disposed for projecting a beam of light normal to said plane of said semiconductor device and said second optical sensor is disposed for receiving an image produced by light from said second light source reflected from said semiconductor device at an acute angle with respect to said plane and said semiconductor device.

14. An inspection apparatus for determining the existence of plural leads on a semiconductor device, the positional accuracy of said leads with respect to a predetermined position of said leads on said semiconductor device and the coplanarity of said plural leads, said apparatus comprising:

a first light source for illuminating said semiconductor device;

a first optical sensor for recording a two dimensional image of said semiconductor device when illuminated by said first light source, said first optical sensor being arranged for projection of said two dimensional image along an axis of said first optical sensor substantially normal to a plane of said semiconductor device;

a second light source operable to project a generally planar beam onto said semiconductor device, said planar beam being generally normal to said plane of said semiconductor device;

a second optical sensor arranged to receive an image of said leads of said semiconductor device generated by reflection of said second light source at an acute angle with respect to said plane of said semiconductor device for determining coplanarity of said leads;

a support for said semiconductor device arranged with respect to said first optical sensor and said second optical sensor for movement of said semiconductor device in a substantially linear path relative to said first optical sensor and said second optical sensor; and control means for causing said first optical sensor and said second optical sensor to record said images while moving said semiconductor device along said path.

15. The apparatus set forth in claim 14 wherein:

said apparatus includes a position sensor operable to determine when said semiconductor device is in a field of view of said first optical sensor for energizing said first light source.

16. The apparatus set forth in claim 15 including:

a sensor operable to determine the position of said support for said semiconductor device and to cause said control means to energize said second light source at least once in response to predetermined relative movement between said semiconductor device, said first optical sensor and said second optical sensor.

17. The apparatus set forth in claim 14 wherein:

said first optical sensor comprises a CCD camera.

18. The apparatus set forth in claim 14 wherein:

said second optical sensor comprises a CCD camera.

19. The apparatus set forth in claim 14 wherein:

said second light source comprises a laser operable to project said planar beam onto said semiconductor device to illuminate plural rows of leads on said semiconductor device wherein said second optical sensor is operable to record images of each of said leads of said plural rows of leads to determine the coplanarity of said leads.

20. The apparatus set forth in claim 14 wherein:

said support for said semiconductor device is operable to change the orientation of said semiconductor device about an axis substantially normal to said plane of said semiconductor device in response to said first optical sensor recording an image of said semiconductor device.

21. The apparatus set forth in claim 14 wherein:

said support is operable to remove said semiconductor device from a first handling media and transport said semiconductor device to a second handling media after said images are recorded by said first optical sensor and said second optical sensor, respectively.

22. The apparatus set forth in claim 21 wherein:

said support for said semiconductor device is operable to transport said semiconductor device to a third handling media in response to comparison of said images recorded by said first optical sensor and said second optical sensor with corresponding predetermined images of said semiconductor device.

23. A system for handling semiconductor devices wherein each of said semiconductor devices includes a plurality of leads thereon, the existence of which and the positional accuracy of which is to be determined, said system including:

a frame including a support for one or more wafer-like substrates, each of said substrates including a plurality of semiconductor devices thereon, each of said semiconductor devices including a plurality of leads formed thereon;

a support member movable relative to said support for said substrates;

an inspection apparatus mounted on said support member for movement relative to said support for said substrates for inspecting the leads on each of said semiconductor devices, said inspection apparatus including a first optical sensor and a first light source for illuminating said semiconductor devices on said substrate to generate a two-dimensional image by said first optical sensor, a second optical sensor and a second light source disposed to project a generally planar beam on to the leads of each semiconductor device to generate a third dimensional image of said semiconductor device by said second optical sensor, said optical sensors and said light sources being spaced from each other to provide for recording a first image by said first optical sensor and a second image by said second optical sensor while moving said inspection apparatus relative to said one or more substrates, said first optical sensor being disposed to record an image projected from a predetermined plane of said semiconductor device and said second optical sensor being disposed to record an image projected at an acute angle with respect to said plane of said semiconductor device for determining the coplanarity of said leads; and a processing unit operably connected to said first and second optical sensors for comparing images recorded thereby, respectively, with information stored in said processing unit for determining one of the existence of leads on said semiconductor device, the positional accuracy of said leads and the coplanarity of portions of said leads.

24. The system set forth in claim 23 wherein:

said apparatus is operable to move in at least two mutually perpendicular directions with respect to said substrate for recording images of each of plural ones of said semiconductor devices on said substrate.

25. A method for inspecting a plurality of leads on a semiconductor device to determine the existence of a predetermined number of said leads, the positional accuracy of said leads and the coplanarity of said leads, comprising the steps of:

provided an apparatus for transporting semiconductor devices, seriatim, from a first handling media to a second handling media for said semiconductor devices, said apparatus including a head for engaging and supporting a semiconductor device and for transporting said semiconductor device from said first handling media to said second handling media along a predetermined path;

providing an inspection apparatus including a first optical sensor for recording a two dimensional image of said semiconductor device and a second optical sensor for recording an image of a third dimension of said semiconductor device, said first optical sensor and said second optical sensor being spaced apart from each other on said inspection apparatus;

illuminating said semiconductor device with a first light source prior to recording said image with said first optical sensor;

illuminating said semiconductor device with a second light source comprising a generally planar beam prior to recording an image of said semiconductor device generated by said planar beam with said second optical sensor; and causing said support for said semiconductor device to move said semiconductor device along said path and with respect to said inspection apparatus to a first position for recording an image by one of said optical sensors and then to a second position for recording an image by the other of said optical sensors.

26. The method set forth in claim 25 including the steps of:

comparing the position of said semiconductor device relative to said second light source with a predetermined image of said semiconductor device and illuminating said semiconductor device at predetermined intervals with said second light source as said semiconductor device passes a plane containing said beam generated by said second light source for recording images of successive rows of leads on said semiconductor device by said second optical sensor.

27. The method set forth in claim 26 including the step of:

comparing the images of said successive rows of leads of said semiconductor device recorded by said second optical sensor to determine if said leads are coplanar.

28. The method set forth in claim 25 including the step of:

rotating said head about an axis to orient said semiconductor device in a predetermined position in response to recording said two dimensional image by said first optical sensor and comparing said recorded image with a predetermined image of said semiconductor device.

29. The method set forth in claim 25 including the step of:

providing a sensor for sensing a position of said semiconductor device with respect to said first optical sensor for energizing said first light source to illuminate said semiconductor device when said semiconductor device is in a predetermined position relative to said first optical sensor.

30. The method set forth in claim 25 including the step of:

providing a sensor operable to determine the position of said semiconductor device relative to said second optical sensor and energizing said second light source at predetermined intervals in response to movement of said semiconductor device to plural predetermined positions of said semiconductor device relative to said second light source and said second optical sensor.

* * * * *